United States Patent
Kreh

(10) Patent No.: US 7,602,481 B2
(45) Date of Patent: Oct. 13, 2009

(54) METHOD AND APPARATUS FOR INSPECTING A SURFACE

(75) Inventor: Albert Kreh, Solms (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 155 days.

(21) Appl. No.: 12/002,718

(22) Filed: Dec. 18, 2007

(65) Prior Publication Data

US 2008/0174780 A1    Jul. 24, 2008

(30) Foreign Application Priority Data

Jan. 18, 2007    (DE) .................. 10 2007 002 711

(51) Int. Cl.
*G01N 21/88* (2006.01)

(52) U.S. Cl. .................. 356/237.2; 356/237.5

(58) Field of Classification Search ............. 356/237.1, 356/237.2, 237.3, 237.4, 237.5
See application file for complete search history.

(56) References Cited

U.S. PATENT DOCUMENTS

| 2005/0134839 A1* | 6/2005 | Kreh et al. ............... 356/237.2 |
| 2005/0168729 A1* | 8/2005 | Jung et al. ............... 356/237.2 |

* cited by examiner

*Primary Examiner*—F. L Evans
(74) *Attorney, Agent, or Firm*—Davidson, Davidson & Kappel, LLC

(57) ABSTRACT

A method and an apparatus for inspecting a surface of a wafer disclosed. At least one incident-light illuminator is provided to illuminate an area of the surface of the wafer in a first and a second illumination mode, in particular a bright-field and a dark-field illumination. At least one image detector is provided to detect an image of the illuminated area. A storage device is used for storing values on the intensity and the color of an optimized illumination of each incident-light illumination mode.

19 Claims, 3 Drawing Sheets

METHOD AND APPARATUS FOR INSPECTING A SURFACE

This claims the benefit of German Patent Application No. DE 10 2007 002 711.9, filed on Jan. 18, 2007 and hereby incorporated by reference herein.

The present invention relates to a method for inspecting a surface, in particular a surface of a wafer, wherein an illumination means and an image detection means are provided, and an area of the wafer is illuminated with at least a first and a second illumination mode.

The present invention further relates to an apparatus for inspecting a surface, in particular a surface of a wafer.

BACKGROUND

In manufacturing defined surface structures, often a plurality of method or processing steps have to be carried out one after the other. The quality of each completed intermediate product substantially affects the end product. This is why it is often necessary to examine the surface of the intermediate products. For example, in semiconductor manufacturing, wafers are sequentially processed during the manufacturing process in a great number of processing steps. As integration densities increase, the requirements as to the quality of the structures formed on the wafers become more stringent. For this purpose it is advantageous if the quality of individual processing steps, such as of lithographical steps, during the manufacturing process and prior to a downstream processing step, can be reliably assessed. Thus, if already after completion of a processing step and prior to completing the manufacturing process, it is determined that a wafer or a structure formed on a wafer is defective, the wafer can be immediately discarded, without the downstream processing steps having to be carried out. The wafer found defective can be separately post-processed until a satisfactory quality is achieved. In this way the efficiency and yield can be increased in semiconductor manufacture.

To inspect such surfaces, in particular, surfaces of wafers, optical devices are particularly suitable. Optical devices are known which are able to identify various structures on the surface of a wafer by means of image detection. Such wafer inspecting devices can operate in various illumination modes. For example, a bright-field illumination is possible by a so-called bright-field arrangement, wherein the surface of a wafer is illuminated and the light reflected from the surface is detected by a camera. A dark-field illumination is possible by a so-called dark-field arrangement, wherein the surface of the wafer is illuminated and the light diffracted by defects, particles and the like on the surface is detected by a camera. A modified dark-field illumination is implemented by the so called advanced dark-field arrangement.

Image recordings in bright-field and dark-field arrangements are of varying significance. For an optimal wafer inspection it is therefore desirable to record images with a wafer inspection device both in a bright-field arrangement and in a dark-field arrangement. To achieve high precision with the detection of defects on the surface of wafers in a dark-field arrangement, a high intensity of the light flashes used for illuminating the surface is desired. For this purpose the incident light illumination means used in the bright-field and dark-field arrangements are stroboscopically operated. They therefore emit relatively short illumination light flashes that are imaged on the surface of the wafer.

As is well known, the precision in such systems can be enhanced by carrying out color matching. To do this in a bright-field arrangement, the camera gain of the recording camera is adjusted in defined color channels, e.g. in the red and blue channels, so that the inspection device is matched with the bright-field illumination to a reference array of a wafer or a reference wafer to a predetermined color. In the dark-field mode, color matching is not possible, however. This is why erroneous detections cannot be avoided in dark-field imaging, when these are due to color deviations.

SUMMARY OF THE INVENTION

An object of the present invention is to provide a method and an apparatus with which errors due to an insufficient or missing color match can be more substantially reduced, in particular also with dark-field imaging.

The present invention provides a method for inspecting a surface, in particular a surface of a wafer, comprising the steps of: detecting a color error of the illumination means in the first and second illumination modes, optimizing an adjustment of the first and second illumination modes, storing intensity and color of the surface to be inspected for the first and second illumination modes separately, and scanning further surfaces while using the optimized adjustment for the first and second illumination modes while taking the color error of the illumination means into account.

The present invention also provides an apparatus for inspecting a surface, in particular a surface of a wafer, comprising at least one incident-light illumination means to illuminate an area of the surface of the wafer in a first and a second illumination mode, in particular a bright-field and a dark-field illumination, at least one image detection means to detect an image of the illuminated area, and a means for storing values on the intensity and the color of an optimized illumination of each incident-light illumination mode.

According to the present invention, a method and an apparatus for inspecting a surface is suggested, wherein a surface area is illuminated with an illumination means while using different illumination modes. An image detection means is used to detect an image of the illuminated area in each illumination mode, and the illumination is separately optimized for each illumination mode. The color and intensity data resulting from the optimization is stored for each illumination mode. These stored values then serve as a basis for the surfaces to be subsequently inspected, such as for an entire lot of surfaces of wafers to be inspected. To do this, the surfaces to be inspected are scanned while using the data on the color and intensity stored for each illumination mode to be applied.

The different illumination modes will result from the arrangement and implementation of the incident-light illumination means and the image detection means.

With this approach it is ensured that the surface to be inspected can be inspected with improved illumination for each illumination mode. At the same time, the time needed for the method is kept short, because the separation is only carried out during the training phase, so that the known machine errors can be taken into account with respect to the color.

The method can also be used to take second-order errors into account, when testing a lot of surfaces to be inspected. In particular, irregular aperture illumination can be taken into account. Each component can be separately compared with the original surface.

In one embodiment of the invention, the data on the intensity and the color stored for each illumination mode can be corrected by known intensity and color values of the inspection means used. This is how color and intensity errors caused by the inspection means can be taken into account.

In case an illumination predominates in terms intensity, it is sufficient to carry out a color match for this illumination mode. Since the data for the intensity and color already exist, color matching can be carried out in a simple manner.

The data stored on the intensity and the color can also be used to create a reference for comparison with the wafer to be inspected. To do this, a representative portion of the wafer is scanned separately with each illumination mode, and a reference is obtained from this scan. This can be done by extracting an illumination component or by comparing the components separately. In either case the color and intensity values corrected by the color and intensity data of the inspection means can be used. A reference image can also be created from the comparison, which is provided for comparison with the remaining wafers of the lot.

A particular advantage of the present invention is that the stored color and intensity data for each illumination mode can be transferred to other inspection means. This is how it is possible to extrapolate these data on the color and intensity data to other inspection means, i.e. to correct the data. As a result a reference image adapted for the other inspection means can also be created. This is why it is also immediately possible to use other inspection means for inspecting the lot of wafers, wherein the wafer is scanned and then compared to the extrapolated reference image.

The illumination means used often have variations in their illumination intensity and/or color. In an embodiment of the present invention, these variations can be taken into account by detecting the varying intensity and/or color of the illumination means with a reference detector and correcting each individual image or each pixel, in particular for each wafer. For this purpose, the reference detector is provided at a suitable position in the beam path of the illumination means.

By separately storing the optimized data on the intensity and color for each illumination mode, it is possible to achieve that when a plurality of images are recorded, the illumination for each of the illumination modes used, such as bright-field illumination, dark-field illumination or advanced dark-field illumination, is optimally adjusted for the wafer to be inspected, so that optimized images can be obtained for each illumination mode of this wafer. In a downstream image processing means, these images can then be evaluated in a particularly useful manner.

BRIEF DESCRIPTION OF THE DRAWINGS

Other advantages and advantageous embodiments of the invention are the subject matter of the following figures and the portions of the description relating thereto, wherein, in particular.

DETAILED DESCRIPTION

Figure 1:
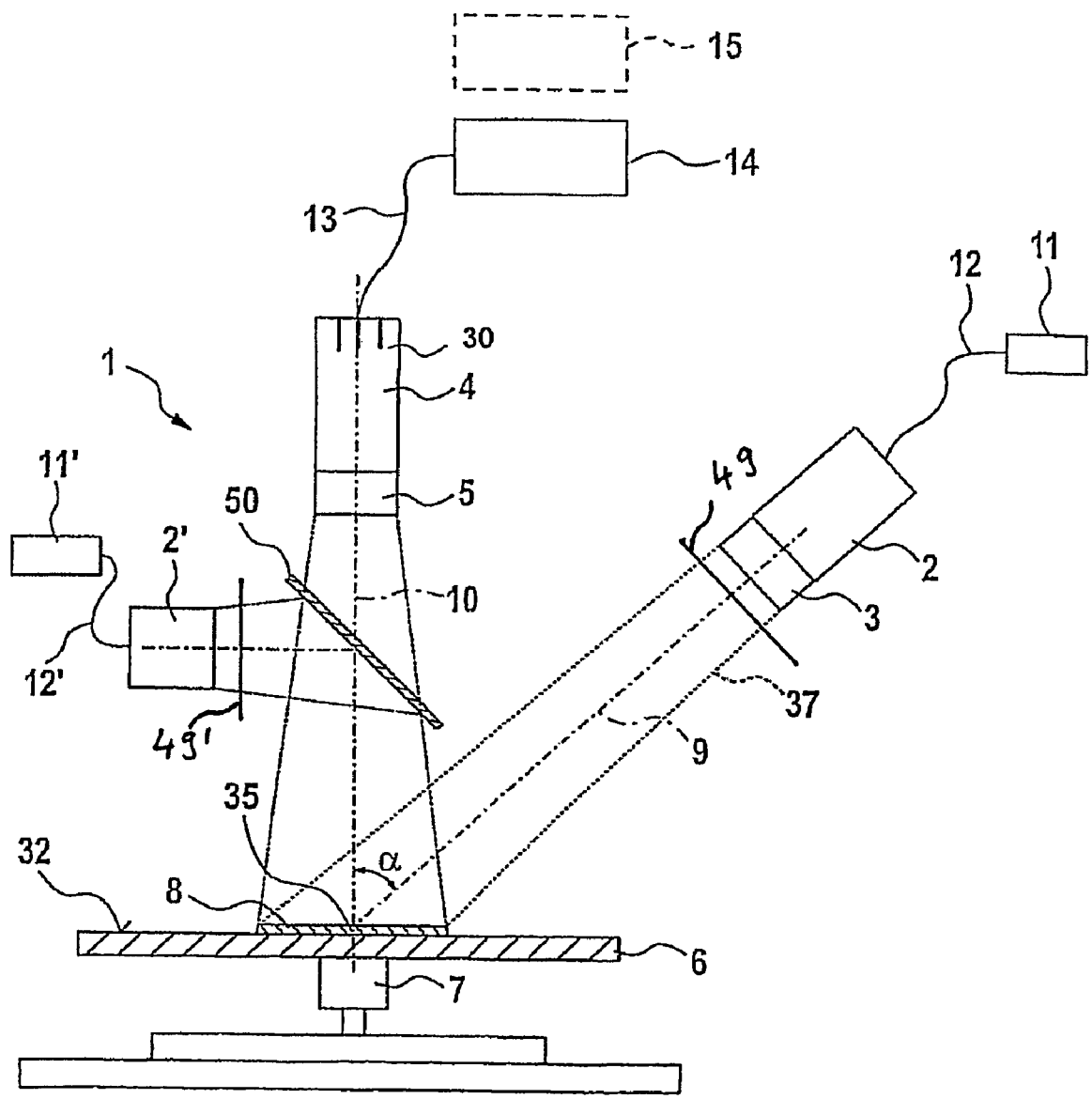
FIG. 1 is a schematic side view of a wafer inspection apparatus.

FIG. 1 shows, in a possible embodiment, a surface to be inspected in a schematic side view. The surface shown here is the surface of a wafer 6 which can be inspected by a wafer inspection apparatus 1. Wafer inspection apparatus 1 comprises two incident-light illumination means 2, 2', each emitting an incident-light illumination light beam 37 in order to illuminate an area 8 on surface 32 of wafer 6. Wafer inspection apparatus 1 further comprises a camera 4 acting as an image detection means, serving to detect an image of the illuminated area 8 on surface 32 of wafer 6. Camera 4 can be implemented as a matrix or line camera for detecting monochromatic and/or color images, preferably with R, G and B color components. Reference numeral 30 schematically denotes the entirety of the color channels of camera 4 suitable for reading out color image data. Imaging axis 10 defined by camera 4 is normal to surface 32 of wafer 6. A lens 5 provided in front of camera 4 images illuminated area 8 onto the image plane of camera 4. The image data detected by camera 4 are read out by a computer 14 acting as a data readout device via data line 13 for storage and/or further processing. Computer 14 may include a memory. The image data can be displayed on an output device, such as a monitor or a display 15. Preferably only one camera 4 is provided, but basically a plurality of cameras 4 can also be provided.

Incident-light illumination means 2 has a light source 11 associated with it, which is fed into incident-light illumination means 2 by means of a light guide or a fiber optic bundle 12. A lens or an objective 3 images incident-light illumination light beam 37 onto surface 32 of wafer 6, but it is not necessarily provided. Incident-light illumination means 2 defines an illumination axis 9 inclined relative to the normal on surface 32 of the wafer or to imaging axis 10 at an angle α.

A second incident-light illumination means 2' has a light source 11' associated with it, the light of which is suitably coupled, such as by means of a light guide or a fiber optic bundle 12', into the incident-light illumination means 2'. The light beam emitted by the incident-light illumination means 2' is reflected by the front surface of a beam splitting mirror 50 onto surface 32 of wafer 6, so that the illumination axis of incident-light illumination means 2' coincides with imaging axis 10 of camera 4.

Incident-light illumination means 2' is arranged in a bright-field arrangement, so that the light reflected by illuminated area 8 on surface 32 of wafer 6 passes through beam splitting mirror 50 and is imaged into camera 4. Incident-light illumination means 2 is arranged in a dark-field arrangement, so that illumination light beam 37 is not directly reflected from surface 32 of wafer 6 into camera 4. Rather, incident-light illumination light beam 37 only images diffracted light, such as due to defects or particles in the illuminated area 8 or deviated light into camera 4.

Wafer 6 is held on a wafer support means 7, such as a vacuum chuck or an electrostatic chuck. Wafer support means 7 is configured in such a way that it is moveable. It is thus ensured that wafer 6 can be moved relative to the incident-light illumination light beams in a continuous or stepped manner. This can be achieved, for example, by rotating wafer 6 about the normal extending through the point of incidence 35 on surface 32 of wafer 6. Wafer 6 can also be displaced in mutually orthogonal spatial directions in the plane of wafer 6 in a translating movement.

Figure 2:
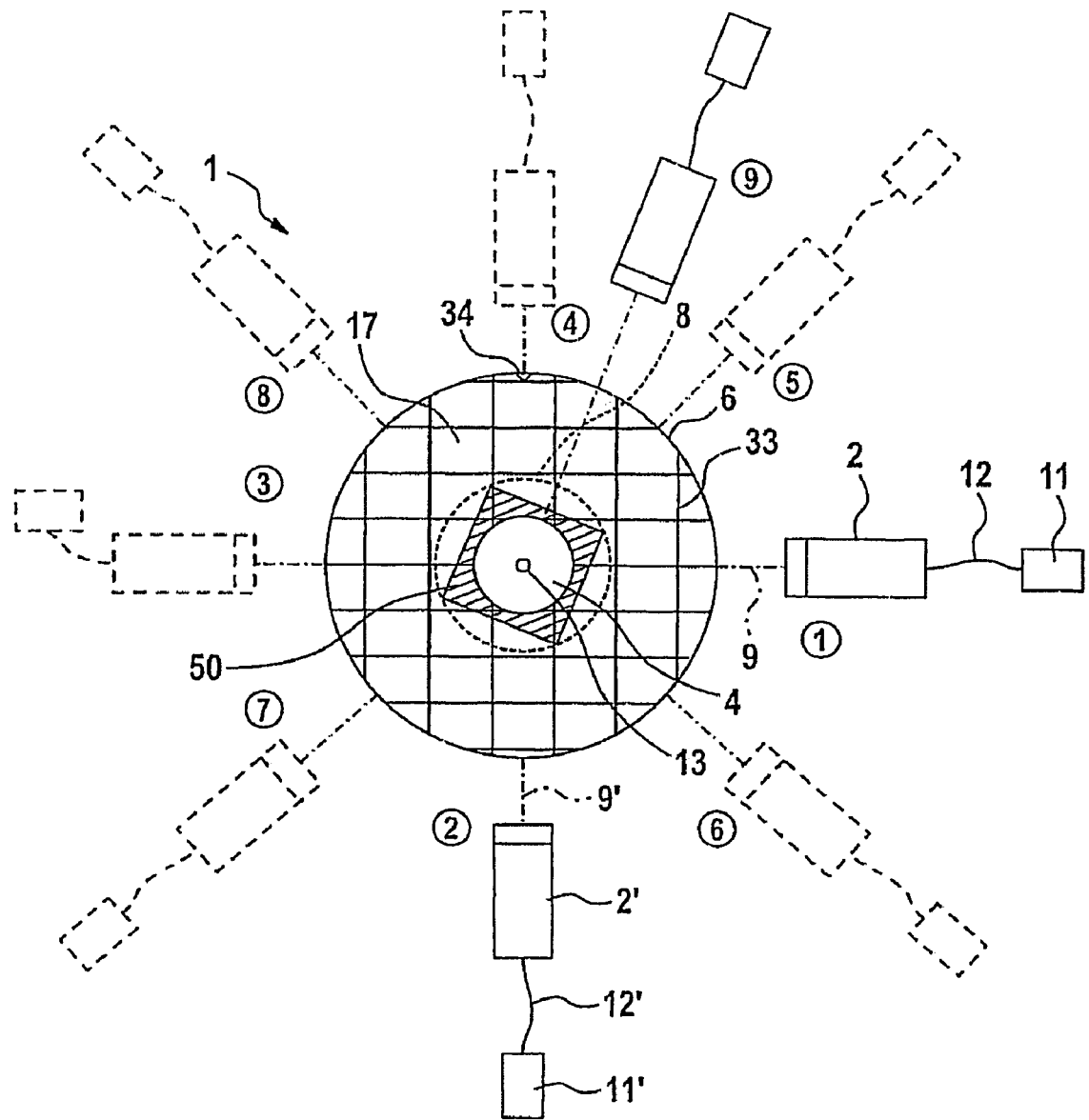
FIG. 2 is a schematic plan view of the wafer inspection apparatus.

FIG. 2 shows a plan view of the wafer inspection apparatus according to FIG. 1. Herein, the two incident-light illumination means 2, 2' are arranged at right angles to each other at two positions indicated by numerals 1 and 2 surrounded by circles. Wafer 6 is held in a predetermined orientation on wafer support means 7. To orient wafer 6, a notch 34, a flat (not shown) or a mark on the surface of wafer 6 is used. To orient wafer 6, a wafer aligner can be provided, or wafer 6 already aligned at a predefined orientation, can be transferred to the wafer support means by means of a grasping arm or the like while maintaining the predetermined orientation.

As shown in FIG. 2, a plurality of dies 17 is formed on the surface of wafer 6, and linear structures 33 preferably intersecting at right angles, for example so-called streets, are formed on the surface of wafer 6. The projections of illumination axes 9, 9' on the surface of wafer 6, extend in parallel or at right angles to linear structures 33 on the surface of wafer 6.

As indicated with broken lines in FIG. 2, further incident-light illumination means can be arranged along the circumference of wafer 6 and are arranged for example at angular intervals relative to incident-light illumination means 2 indicated by numeral 1, the intervals preferably corresponding to an integer multiple of 45° or 90°. These possible positions are indicated by numerals 3 through 8 in circles in FIG. 2.

Camera 4 is arranged on the normal to the surface of wafer 6 in order to detect diffracted light from the surface of wafer 6 originating from the illumination by one of the incident-light illumination means indicated with numerals 1 through 8.

Another incident-light illumination means is arranged at the position indicated with numeral 9 for emitting a light beam essentially parallel to the surface of wafer 6. This light beam, as shown in FIG. 1, is reflected by the front surface of beam splitting mirror 50 in a direction vertical to the surface of wafer 6. Incident-light illumination means 2 arranged at the positions indicated by numerals 1 through 8 are arranged in a dark-field arrangement. Incident-light illumination means 2 arranged at the position indicated by numeral 9 is arranged in a bright-field arrangement.

Figure 3:
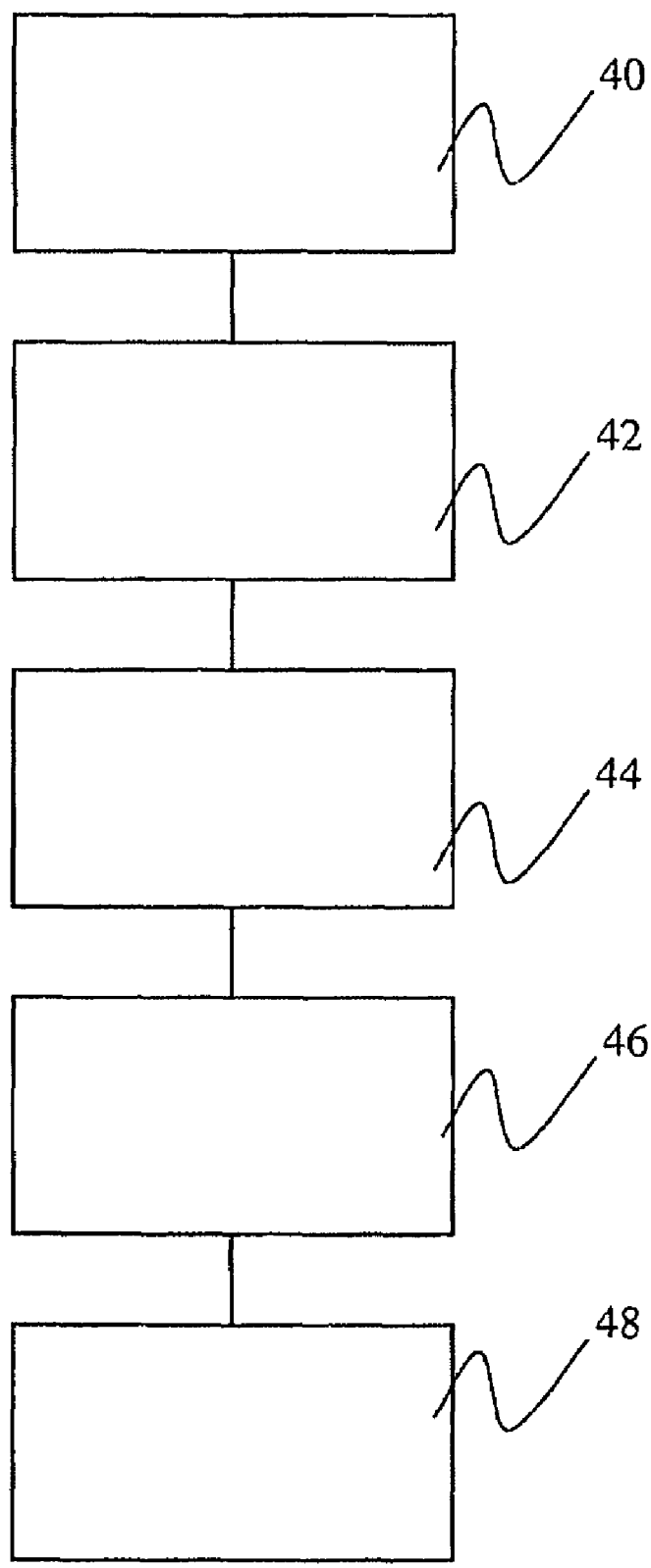
FIG. 3 schematically shows the operating sequence of the method according to the present invention.

The process steps for carrying out the method according to the present invention with wafer inspection apparatus 1 according to FIG. 1 or 2 is schematically illustrated in FIG. 3.

Before wafer inspection apparatus 1 scans the surfaces of a number of equivalent wafers 6, the illuminations for the bright-field illuminations and dark-field illuminations are optimized in optimization step 40. To do this, the illumination for each of the bright-field and dark-field illuminations used is varied in their intensity in such a way that an optimal imaging is achieved. These values depend on structure 33 and the structure of the dies 17, i.e. on the morphology of wafer 6. For this purpose, a reference, preferably a reference array of the surface or a reference surface, such as a reference wafer, is used. The illumination of the reference allows the color error of the illumination means to be obtained separately for each illumination mode.

If required, these values are corrected and the thus obtained values on the intensity and color are stored for each illumination mode of wafer inspection apparatus 1 in storing step 42. These values result from the fact that the wafer is only ever illuminated by one illumination means and the brightness values and the color values for this illumination are stored in the recipe. Usually the light sources of the incident-light illumination means used for the bright-field illumination and the dark-field illumination are polychromatic and therefore provided with a plurality of color channels. However, monochromatic light flashes of different colors may also be used for bright-field illumination 2' and dark-field illumination 2. For example, a blue light flash may be used for bright-field illumination 2' and a polychromatic or a light flash having any other than the blue color may be used for dark-field illumination 2. Monochromatic illumination light flashes may further be used for color separation, using different colors for imaging in a bright-field arrangement and for imaging in a dark-field arrangement. Also for these cases, the color and intensity values of each illumination mode may be separately stored, as explained above.

As a result, wafer inspection apparatus 1 has been measured and adjusted with respect to the reference. The improved data for illumination has been stored. The surfaces of a number of equivalent wafers can now be scanned using wafer inspection apparatus 1. The stored data are used for each illumination.

After storing the color and intensity values in step 42 they may optionally be modified with color and intensity values known from wafer inspection apparatus 1 used, in machine data step 44 and stored if necessary. This allows the individual machine data to be taken into account.

For operating wafer inspection apparatus 1 and therefore for detecting the surface of wafer 6, the stored data on the color and intensity are used in the associated incident-light illumination means 2, 2' and surface 32 of wafer 6 is scanned in scanning step 46. Incident-light illumination means 2, 2' are stroboscopically operated, in order to emit short light flashes, such as with a flash duration of about 15 microseconds, with the stored color and intensity values onto the surface of wafer 6. Between light flashes, wafer 6 is displaced in a continuous manner, according to an alternative embodiment also in a stepped and synchronous manner, relative to the imaging means, so that images of areas periodically offset with respect to each other may be detected on the wafer surface, and eventually the entire wafer surface is sequentially sampled. Subsequently, a new exposure cycle is started. The images of illuminated area 8 on surface 32 of wafer 6 detected by camera 4 are read out in synchronism with the illumination light flashes, such as by a frame grabber card, and passed on to a computer, where the image data are intermediately stored and/or further processed. The evaluated images are shown on monitor 15.

Optionally color matching can be carried out in color matching step 48, wherein it is checked whether an illumination mode dominates in brightness. If this is the case, the color match is only carried out for this illumination mode. To do this, the camera gain of camera 4 used for imaging is adjusted in relevant channel 30 in such a way that wafer inspection apparatus 1, in the corresponding illumination mode, is matched with a reference array of a wafer 6 or with a reference wafer to a predetermined color.

Further advantages can be achieved for each illumination mode by storing color and intensity data resulting from the optimization in the manner according to the present invention. The stored color and intensity data may thus be transferred to another surface inspection apparatus, in particular to another wafer inspection apparatus. This is how the individual components of the illumination of each illumination mode can be extrapolated with the known color and intensity data of this apparatus. This is why a relevant adapted reference image is provided for the other apparatus in a simple manner. When scanning wafer 6, the results will be compared with the extrapolated reference image. To generate the reference image, each component must be calculated accordingly. If the camera has a non-linear characteristic, an averaged intensity curve for camera type 4 may also be utilized. For a more precise evaluation, the intensity curve of camera 4 may also be measured and the reference image may be obtained taking this intensity curve into account, which may also be prestored.

In a further embodiment of the invention, the resulting color and intensity data may be used for each illumination mode also for scanning wafer 6 to generate an improved reference. For this purpose, prior to and after scanning of the first wafer of a lot, a representative portion of wafer 6 may be separately scanned with each illumination mode. With this scan, the individual components of the illumination modes may be separated, corrected with the machine data, and an improved reference image may be created, which will be used for comparison with all remaining wafers of the lot. Moreover, one or more illumination components may be extracted and only the remaining illumination component may then be compared with the reference data from the recipe.

The precision of the method according to the present invention and the apparatus according to the present invention may be further enhanced by compensating any occurring variations of the incident-light illumination sources 2, 2' in their intensity and color. For this purpose, the varying intensity and color of the illumination means may be detected for instance by providing a reference detector 49, 49' in the beam path of incident-light illumination source 2, 2'. This is how each intensity and color of the individual light flashes of each illumination means may be detected and each individual image may be suitably corrected using the known coupling factors.

The correction described, which is achieved by storing and reusing the stored color and intensity values of the individual illumination modes, may also be used solely in the color analysis of wafer 6, of the individual images, or for each pixel.

While the method and apparatus according to the present invention have been described with reference to the figures in an exemplary manner as relating to surfaces of a wafer, it is not limited to such semiconductor surfaces. Rather, both may also be used for inspecting surfaces of other workpieces. The method may be used particularly advantageously with such workpieces where the inspection of a lot of similar workpieces is carried out.

What is claimed is:

1. A method of inspecting a surface of a wafer using an illuminator and an image detector, and an area of the wafer is illuminated with at least a first and a second illumination mode, comprising the steps of:
    detecting a color error of the illuminator in the first and second illumination modes;
    optimizing an adjustment of the first and second illumination modes;
    storing intensity and color of the surface to be inspected for the first and second illumination modes separately; and
    scanning further surfaces while using optimized adjustment for the first and second illumination modes while taking the color error of the illuminator into account.

2. The method according to claim 1, wherein a color match is carried out for at least one of the illuminator.

3. The method according to claim 1, wherein the first illumination mode is a bright-field illumination and the second illumination mode is a dark-field illumination.

4. The method according to claim 1, wherein the second or a further illumination mode is an advanced dark-field illumination.

5. The method according to claim 1, wherein the data on the intensity and color for each of the first and second illumination modes is corrected by known intensity and color values of an inspection device used.

6. The method according to claim 5, wherein a color match is carried out for the first or second illumination mode which dominates in terms of intensity.

7. The method according to claim 1, wherein a representative portion of the wafer is separately scanned with each of the first and second illumination modes and a reference for the further work pieces is generated from the scan.

8. The method according to claim 1, wherein the wafer with an extracted illumination component is compared with the reference, and/or with each illumination component separately, is compared with the reference, and a reference image is generated from the comparison.

9. The method according to claim 1, wherein the stored data on the intensity and the color of an inspection device having the illuminator, and, if applicable, the scan data on the representative area of wafer is transferred to a second inspection device, and the transferred data on the intensity and the color is corrected within the second inspection device by known intensity and color values of the second inspection device, and a reference adapted to the second inspection device is generated, if necessary, from these data.

10. The method according to claim 1, wherein a second illuminator is provided for a second wafer, and wherein a varying intensity and/or color of the first and/or second illuminator is detected with a reference detector, and each individual image or each pixel is corrected for each of the first and second wafers.

11. The method according to claim 1, wherein the step of detecting the color error of the illuminator is carried out on a reference.

12. The method according to claim 11, wherein the reference includes an inbuilt reference array or a reference surface.

13. An apparatus for inspecting a surface of a wafer, comprising:
    at least one incident-light illuminator to illuminate an area of the surface of the wafer in a first and a second illumination mode, and at least one image detector to detect an image of the illuminated area, and a storage device for storing values on intensity and color of an optimized illumination of each of the first and second illumination modes.

14. The apparatus according to claim 13, wherein the first illumination mode is a bright-field illumination mode and the second illumination mode is a dark-field illumination mode.

15. The apparatus according to claim 13, wherein the at least one illuminator includes a first incident-light illuminator arranged in such a way that images of the illuminated area are detectable in a bright-field arrangement, and a second incident-light illuminator arranged in such a way that images of the illuminated area are detectable in a dark-field arrangement.

16. The apparatus according to claim 13, wherein a reference detector for detecting the varying intensity and color of the illuminator is provided in a beam path of the illuminator.

17. The apparatus according to claim 16, wherein a color filter is provided in the beam path of the illuminator.

18. The apparatus as recited in claim 13, wherein the illuminator includes a light source.

19. An apparatus for inspecting a surface of a wafer, comprising:
    at least one incident-light illumination means to illuminate an area of the surface of the wafer in a first and a second illumination mode, and at least one image detector to detect an image of the illuminated area, and means for storing values on intensity and color of an optimized illumination of each of the first and second illumination modes.

* * * * *